US012766178B2

(12) United States Patent
Johnson

(10) Patent No.: US 12,766,178 B2
(45) Date of Patent: Oct. 20, 2026

(54) SKIN CLARIFIER

(71) Applicant: Johnson Consulting, LLC, San Juan, PR (US)

(72) Inventor: Benjamin Johnson, Evergreen, CO (US)

(73) Assignee: JOHNSON CONSULTING, LLC, San Juan, PR (US)

( * ) Notice: Subject to any disclaimer, the term of this patent is extended or adjusted under 35 U.S.C. 154(b) by 0 days.

(21) Appl. No.: 17/451,109

(22) Filed: Oct. 15, 2021

(65) Prior Publication Data

US 2022/0118038 A1 Apr. 21, 2022

Related U.S. Application Data

(60) Provisional application No. 63/198,416, filed on Oct. 16, 2020.

(51) Int. Cl.

| | |
|---|---|
| ***A61K 36/34*** | (2006.01) |
| ***A23L 33/105*** | (2016.01) |
| ***A61K 8/9789*** | (2017.01) |
| ***A61K 36/28*** | (2006.01) |
| ***A61K 36/68*** | (2006.01) |
| ***A61K 36/80*** | (2006.01) |
| ***A61K 45/06*** | (2006.01) |
| ***A61Q 19/00*** | (2006.01) |

(52) U.S. Cl.
CPC ............ *A61K 36/34* (2013.01); *A23L 33/105* (2016.08); *A61K 8/9789* (2017.08); *A61K 36/28* (2013.01); *A61K 36/68* (2013.01); *A61K 36/80* (2013.01); *A61K 45/06* (2013.01); *A61Q 19/00* (2013.01); *A61K 2800/591* (2013.01); *A61K 2800/92* (2013.01)

(58) Field of Classification Search
None
See application file for complete search history.

(56) References Cited

U.S. PATENT DOCUMENTS 6,210,738 B1 * 4/2001 Chen .................... A23L 33/105 426/590
2003/0018009 A1 * 1/2003 Collins .................. A23L 7/101 514/52

* cited by examiner

*Primary Examiner* — Susan Hoffman
(74) *Attorney, Agent, or Firm* — Trenner Law Firm, LLC; Mark Trenner

(57) ABSTRACT

An example skin clarifier supplement including a synergistic combination of lobelia herb powder, plantain leaf powder, mullein leaf powder, ellecampane root powder and serrapeptase. Each component is provided in an effective dose to serve as an anti-inflammatory agent for treatment of skin conditions. In an example, the effective dose is about equal proportions by weight of the lobelia herb powder, the plantain leaf powder, the mullein leaf powder, the ellecampane root powder and the serrapeptase.

10 Claims, 12 Drawing Sheets
(11 of 12 Drawing Sheet(s) Filed in Color)

Fig. 2
Before
before cleanse after starting stemfactor
After Osmosis candida cleanse

SKIN CLARIFIER

PRIORITY CLAIM

This application claims the priority filing benefit of U.S. Provisional Patent Application No. 63/198,416 filed Oct. 16, 2020 of Benjamin Johnson for "Skin Clarifier" hereby incorporated by reference for all that is disclosed as though fully set forth herein.

BACKGROUND

Researchers and physicians have been attempting to solve the challenges of many skin conditions by using medications that target suspected bacterial infections like antibiotics or by treating presumed immune system irregularities (excess inflammation) with immunomodulators or steroids. Both of these options come with health consequences and side effects and often do not result in a successful outcome.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
FIGS. 1-11 are photographs showing before treatment (left) and after treatment (right).
Figure 2:
Figure 3:
Figure 4:
Figure 5:
Figure 6:
Figure 7:
Figure 8:
Figure 9:
Figure 10:
Figure 11:

A skin clarifier is disclosed herein. In an example, the skin clarifier includes a combination of herbs to be taken internally as an oral supplement for conditions such as, but not limited to, acne, allergies, eczema, psoriasis, seborrheic dermatitis, sebaceous hyperplasia, syringoma, yeast infections, chronic constipation, inflammatory bowel syndrome, blackheads, and bloating, to name only a few examples.

Such conditions are treatable through internal mechanisms explained herein. The skin clarifier may include, but is not limited to including: 1) Lobelia herb powder, 2) Plantain leaf powder, 3) Mullein leaf powder, 4) Ellecampane root powder and 5) Serrapeptase. Each individual component of the skin clarifier disclosed herein can be used with some success. But more of these components used in combination leads to better and faster results. The skin clarifier when ingested for the identified skin conditions is a novel approach and a completely different direction than where medicine and medical research has gone in the past.

Before continuing, it is noted that as used herein, the terms "includes" and "including" mean, but is not limited to, "includes" or "including" and "includes at least" or "including at least." The term "based on" means "based on" and "based at least in part on."

It is also noted that the examples described herein are provided for purposes of illustration, and are not intended to be limiting. Other devices and/or device configurations may be utilized to carry out the operations described herein.

The operations shown and described herein are provided to illustrate example implementations. It is noted that the operations are not limited to the ordering shown. Still other operations may also be implemented.

In an example, the skin clarifier is an oral supplement. The supplement may include a synergistic combination of lobelia herb powder, plantain leaf powder, mullein leaf powder, ellecampane root powder and serrapeptase, each in an effective dose to serve as an anti-inflammatory agent for treatment of skin conditions. In an example, the effective dose is about equal proportions by weight of the lobelia herb powder, the plantain leaf powder, the mullein leaf powder, the ellecampane root powder and the serrapeptase.

In an example, sesquiterpene lactones work synergistically to reduce inflammation in the human body.

In an example, mullein leaf powder contains saponins, iridoid glycoside, phenylethanoid glycoside, and flavonoids that work synergistically to reduce inflammation in the human body.

In an example, the supplement includes an iridoid glucoside that works synergistically to reduce inflammation in the human body. For example, the iridoid glucoside may be aucubin.

In an example, the supplement includes active alkaloids that work through activation of Dopamine D1 receptors. For example, the active alkaloids may include lobeline and lobenaline.

FIGS. 1-11 are photographs showing before treatment (left) and after treatment (right). The photographs each show use of the oral supplement for treatment of a skin condition, such as acne. It is noted, however, that the supplement described herein may also be formulated to treat other conditions.

By way of example, the lobelia leaf herb helps with smoking cessation and has known respiratory benefits including asthma, bronchitis, and some breathing related issues. It can be helpful in dealing with skin inflammation, an aspect of acne. The mechanism of action is thus far unexplainable. Lobeline and lobenaline the key active alkaloids in this herb that appear to work through the activation of Dopamine D1 receptors.

The plantain leaf (raw leaves and the oil they secrete) are anti-inflammatory when rubbed on the skin. Internally as a powdered herb, it has also shown some respiratory and possibly pain relief benefits. When ingested, the supplement contributes to the improvement of the skin conditions listed herein. Aucubin, an iridoid glucoside as the main active ingredient involved in this herb, acts as an anti-inflammatory agent for treating the skin conditions.

The mullein leaf herb is primarily found to be beneficial for respiratory illnesses and colds, with some noted gastrointestinal benefits as well. When ingested as part of a treatment plan, it contributes to improvement of the skin conditions. Mullein contains several anti-inflammatories including saponins, iridoid and phenylethanoid glycosides and flavonoids that work synergistically with the other herbs to assist in treating the skin conditions.

The elecampane root herb is primarily associated with respiratory conditions including coughs, asthma and whooping cough. When ingested as a part of the supplement, it contributes to treating the improvement of the skin conditions. The key actives in this herb are the sesquiterpene lactones that act as an anti-inflammatory, especially in combination with the other herbs, for treating the skin conditions.

The serrapeptase proteolytic enzyme is used for sinus related conditions and sometimes for liver health. When ingested as a part of the supplement, it contributes to treating the improvement of the skin conditions. This ingredient has proven to have anti-inflammatory properties.

Acne has confounded medical professionals focused on the cause being bacterial or based on an oil plug leading to a bacterial infection. There are other unknown components to this skin condition that are indirectly improved by the supplement.

Eczema is a skin condition. Most pharmaceutical research points to auto-immune activity at the skin level, meaning that the skin is "attacking" itself. The medications approved for treatment seek to suppress this excess immune activity thereby calming the ongoing damage. Topical applications of plantain leaf may offer modest soothing to eczema. Each individual component of the skin clarifier disclosed herein, both combined together and used individually, indirectly reduce inflammation and help clear the appearance of this skin condition when ingested as part of the supplement.

Psoriasis is a skin condition. This condition is known for the rapid build-up of skin cells causing scaling and peeling that are all related to the body attacking itself according to current Western medical research. The medications approved for treatment seek to suppress this excess immune activity thereby calming the ongoing damage. Each individual component of the skin clarifier supplement, both combined together and used individually, indirectly treat the appearance of this skin condition when ingested.

Seborrheic Dermatitis is a skin condition. It is known for causing skin to peel, and secrete oil. The medications approved for treatment seek to suppress this excess immune activity thereby calming the ongoing damage. Each individual component of the skin clarifier supplement, both combined together and used individually, indirectly treat the appearance of this skin condition and can heal when ingested.

Syringoma is a skin condition. It is known for having hard nodules (tumors) under the skin that relate to sebaceous gland activity in some way. There is no approved medication for this condition. Physicians often prescribe topical acids, surgery, laser cautery and other methods to burn, remove or break apart the tumor. Each individual component of the skin clarifier supplement, both combined together and used individually, indirectly treat the appearance of this skin condition when ingested.

Allergies are an overreaction by the immune system that results in congestion, itching and watery eyes, activation of histamine pathways and all the symptoms that can entail. These symptoms are activated by allergens. Successful allergy therapies include micro dosing the allergen into the system and suppression of the immune system's hyperactive response using various approved medications and over the counter (OTC) remedies. Each individual component of the skin clarifier supplement, both combined together and used individually, indirectly treat the appearance of this skin condition when ingested. It improves both the allergy symptoms and associated skin conditions.

Yeast infections have been associated with changes in body pH, hormonal imbalances, and microbiome alterations often related to antibiotic therapy. One or more of the components of the skin clarifier supplement benefits women with yeast infections in most cases. Yeast infections relate to inflammation associated with toxins and proteins that yeast excrete, and the supplement helps the body reduce those symptoms.

Sebaceous Hyperplasia is believed by most scientists and physicians to be an auto-immune condition of unknown origin. It is sometimes treated with topical antibiotics or steroids. Sometimes it is treated with excision or laser or other methods designed to burn or destroy the sebaceous gland. It has been suggested there is an androgen component to the conditions because of the connection with increased sebum and gland activity. This enlarged sebaceous gland has an inflammatory component that is improved by the supplement. Each individual component of the skin clarifier supplement, both combined together and used individually, indirectly treat the appearance of this skin condition when ingested.

Inflammatory Bowel Disease is not well understood, but relates to either an infection of the digestive mucosa, an allergic reaction to a food or ingredient or other factors related to hyperactivity of the immune system. The treatment mostly involves immunomodulators, antibiotics, steroids or other medications designed to inhibit the immune hyperactivity. Each individual component of the skin clarifier supplement, both combined together and used individually, indirectly treats the appearance of this skin condition when ingested.

Figure 12:
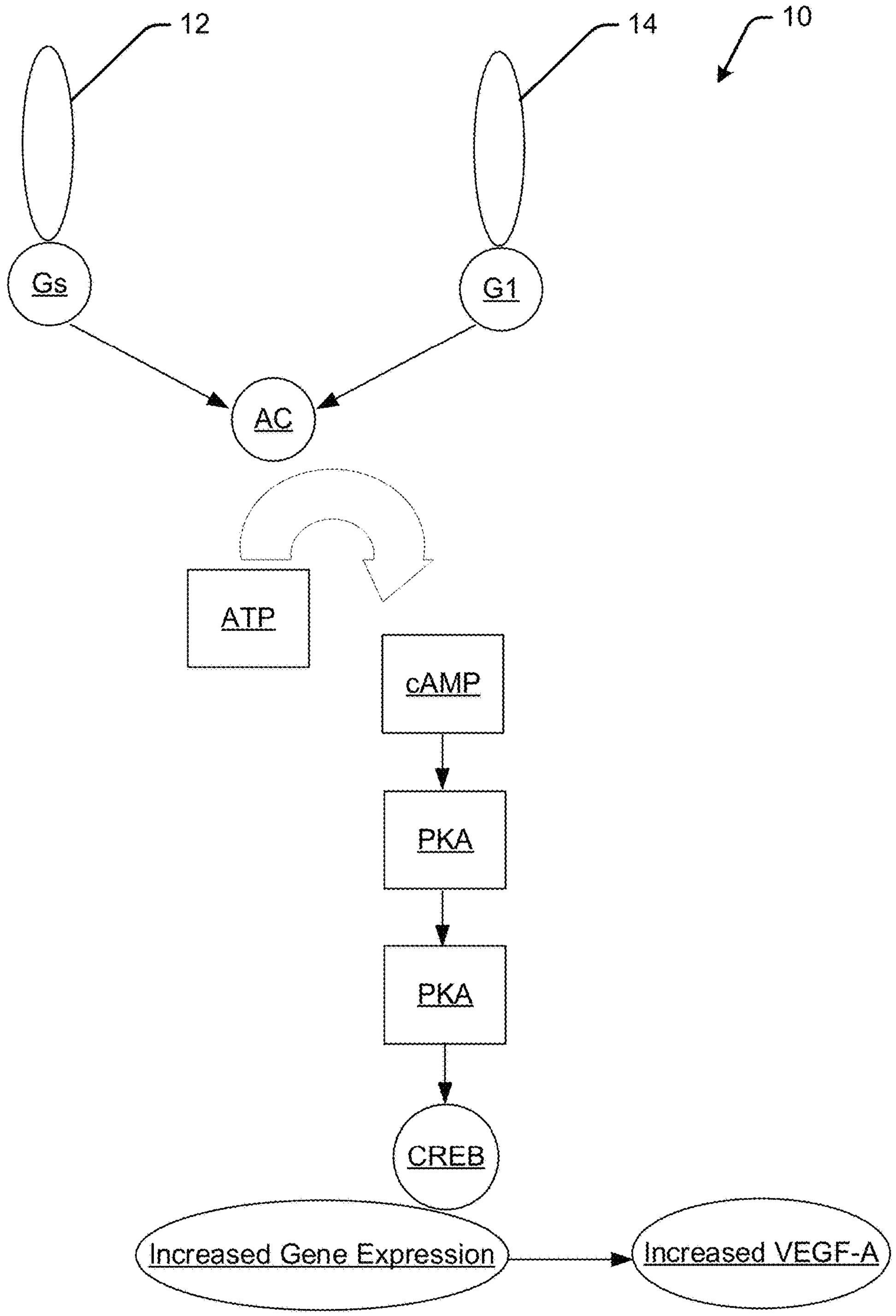
FIG. 12 is a schematic diagram illustrating a treatment mechanism according to the disclosure herein.

FIG. 12 is a schematic diagram illustrating a treatment mechanism 10 according to the disclosure herein. In the figure, the D1 Receptor (D1, D5) is illustrated by reference 12 and the D2 Receptor (D2, D3, D4) is illustrated by reference 14. The D1 Receptor Agonism improves the rate of wound closure, increases angiogenesis, increases cAMP level, and increases VEGF expression by human dermal fibroblasts. The D2 Receptor Agonism decreases the rate of wound closure, decreases angiogenesis, decreases epidermal hyperplasia, and decreases cAMP levels. The D2 Receptor Antagonism increases MSC mobilization into wound beds.

It is noted that the examples shown and described are provided for purposes of illustration and are not intended to be limiting. Still other examples are also contemplated.

The invention claimed is:

1. A skin clarifier oral dietary supplement comprising an anti-inflammatory agent to be taken internally having a combination of lobelia herb powder, plantain leaf powder, and mullein leaf powder each provided in an effective dose of about equal proportions by weight for treatment of skin conditions, and alkaloids that work through activation of Dopamine D1 receptors, wherein the oral supplement is in the form of at least one of pills, tablets, capsules, gummies, and softgels.

2. The skin clarifier oral dietary supplement of claim 1, wherein sesquiterpene lactones reduce inflammation in the human body.

3. The skin clarifier oral dietary supplement of claim 1, wherein mullein leaf powder contains saponins, iridoid glycoside, phenylethanoid glycoside, and flavonoids that reduce inflammation in the human body.

4. The skin clarifier oral dietary supplement of claim 1, further comprising an iridoid glycoside that reduces inflammation in the human body.

5. The skin clarifier oral dietary supplement of claim 4, wherein the iridoid glycoside is aucubin.

6. The skin clarifier oral dietary supplement of claim 1, wherein the active alkaloids include lobeline and lobenaline.

7. The skin clarifier oral dietary supplement of claim 1, further comprising elecampane root powder and serrapeptase and the effective dose is about equal proportions by weight of the lobelia herb powder, the plantain leaf powder, the mullein leaf powder, the elecampane root powder and the serrapeptase.

8. A skin clarifier oral dietary supplement comprising:

an oral supplement having an effective dose of lobelia herb powder, plantain leaf powder, mullein leaf powder, elecampane root powder and serrapeptase; and active alkaloids selected for the oral supplement to work through activation of Dopamine D1 receptors;

wherein the active alkaloids are at least lobeline and lobenaline;

wherein the components provide an anti-inflammatory agent for treatment of skin conditions;

wherein each of the components are provided in the oral supplement in substantially equal proportions by weight;

wherein the oral supplement is in the form of at least one of pills, tablets, capsules, gummies, and softgels.

9. The skin clarifier oral dietary supplement of claim 8, wherein taking the oral supplement internally further treats at least one of acne, allergies, eczema, psoriasis, seborrheic dermatitis, sebaceous hyperplasia, syringoma, yeast infections, chronic constipation, inflammatory bowel syndrome, blackheads, and bloating.

10. The skin clarifier oral dietary supplement of claim 1, wherein taking the oral supplement internally further treats at least one of acne, allergies, eczema, psoriasis, seborrheic dermatitis, sebaceous hyperplasia, syringoma, yeast infections, chronic constipation, inflammatory bowel syndrome, blackheads, and bloating.

* * * * *